(12) United States Patent
Kim et al.

(10) Patent No.: US 10,390,779 B2
(45) Date of Patent: Aug. 27, 2019

(54) X-RAY IMAGING APPARATUS AND CONTROL METHOD THEREOF

(71) Applicant: SAMSUNG ELECTRONICS CO., LTD., Suwon-si (KR)

(72) Inventors: Han Myoung Kim, Suwon-si (KR); Hyun-Sun Kim, Hwaseong-si (KR); Jee Hae Kim, Goyang-si (KR); Sung Nam Kim, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 409 days.

(21) Appl. No.: 15/397,155

(22) Filed: Jan. 3, 2017

(65) Prior Publication Data

US 2017/0196525 A1 Jul. 13, 2017

(30) Foreign Application Priority Data

Jan. 8, 2016 (KR) .................. 10-2016-0002678

(51) Int. Cl.
*A61B 6/00* (2006.01)
*A61B 90/00* (2016.01)
*A61B 6/04* (2006.01)
*A61B 6/06* (2006.01)

(52) U.S. Cl.
CPC ............... *A61B 6/463* (2013.01); *A61B 6/04* (2013.01); *A61B 6/465* (2013.01); *A61B 6/467* (2013.01); *A61B 6/54* (2013.01); *A61B 90/39* (2016.02); *A61B 6/06* (2013.01); *A61B 2090/3937* (2016.02); *A61B 2090/3966* (2016.02)

(58) Field of Classification Search
CPC .... A61B 2090/3937; A61B 2090/3966; A61B 6/04; A61B 6/06; A61B 6/463; A61B 6/465; A61B 6/467; A61B 6/54; A61B 90/39

See application file for complete search history.

(56) References Cited

U.S. PATENT DOCUMENTS

| | | | |
|---|---|---|---|
| 6,542,579 B1 * | 4/2003 | Takasawa | A61B 6/00 378/162 |
| 2009/0021476 A1 | 1/2009 | Steinle et al. | |
| 2009/0240137 A1 | 9/2009 | Rosa | |
| 2015/0250433 A1 | 9/2015 | Hyde et al. | |

* cited by examiner

*Primary Examiner* — Dani Fox
(74) *Attorney, Agent, or Firm* — Sughrue Mion, PLLC

(57) ABSTRACT

An X-ray imaging apparatus includes an X-ray source configured to generate X-rays, and to irradiate the X-rays; an imaging unit configured to photograph an object image; a controller configured to acquire object direction information from the object image, and to determine whether the object direction information corresponds to information about an irradiation direction of X-rays; and a user interface configured to output a warning if the object direction information does not correspond to the information about the irradiation direction of X-rays.

22 Claims, 20 Drawing Sheets

LEFT HAND PA

RIGHT HAND AP

HEAD AP

HEAD PA

X-RAY IMAGING APPARATUS AND CONTROL METHOD THEREOF

CROSS-REFERENCE TO RELATED APPLICATION

This application claims priority from Korean Patent Application No. 10-2016-0002678, filed on Jan. 8, 2016 in the Korean Intellectual Property Office, the disclosure of which is incorporated herein by reference in its entirety.

BACKGROUND

1. Field

Embodiments of the present disclosure relate to an X-ray imaging apparatus having a camera, and a control method thereof.

2. Description of the Related Art

An X-ray imaging apparatus is used to irradiate X-rays onto an object and to analyze X-rays transmitted through the object to thus acquire information about the inside structure of the object. The X-ray imaging apparatus can image the inside structure of the object using a fact that different tissues in the object have different attenuation coefficients obtained by digitizing degrees to which the respective tissues absorb or transmit X-rays.

However, if a patient's left-right direction is wrongly recognized upon diagnosis based on an X-ray image, a misdiagnosis or a medical accident may occur. Accordingly, a patient's direction information in an X-ray image is very important information. However, due to the transmission characteristics of X-rays and the bilateral symmetry of the human body, it is difficult to distinguish a patient's front, back, left, and right body parts from an X-ray image.

SUMMARY

Therefore, it is an aspect of the present disclosure to provide an X-ray imaging apparatus which is capable of providing a patient's direction information corresponding to an X-ray image by photographing the patient's image through a camera, acquiring the patient's direction information from the patient's image or receiving the patient's direction information from a user, and outputting a warning for the user if the patient's direction information does not correspond to an X-ray imaging protocol, and a method of controlling the X-ray imaging apparatus.

Additional aspects of the disclosure will be set forth in part in the description which follows and, in part, will be obvious from the description, or may be learned by practice of the disclosure.

In accordance with one aspect of the present disclosure, an X-ray imaging apparatus includes an X-ray source configured to generate X-rays, and to irradiate the X-rays; an imaging unit configured to photograph an object image; a controller configured to acquire object direction information from the object image, and to determine whether the object direction information corresponds to information about an irradiation direction of X-rays; and a user interface configured to output a warning if the object direction information does not correspond to the information about the irradiation direction of X-rays.

The controller recognizes an object from the object image, and acquires the object direction information including at least one of an up direction, a down direction, a left direction, a right direction, a front direction, a rear direction, and a lateral direction of the object determined based on a feature of the recognized object.

The user interface includes at least one of a display unit configured to output the warning visually, and a speaker configured to output the audible warning.

The information about the irradiation direction of X-rays includes at least one of anteroposterior, posteroanterior, and lateral.

If the object direction information corresponds to the information about the irradiation direction of X-rays, the controller controls the X-ray source to photograph an X-ray image.

The controller displays a marker indicating a direction of the object in the X-ray image, based on the object direction information.

The user interface includes a display unit configured to display the X-ray image, and an input unit configured to receive an input for displaying a marker indicating a direction of the object in the X-ray image.

If the direction of the object indicated by the marker does not correspond to the object direction information, the controller outputs a warning through the display unit.

In accordance with one aspect of the present disclosure, an X-ray imaging apparatus includes an X-ray source configured to generate X-rays, and to irradiate the generated X-rays; an imaging unit configured to photograph an object image; a display unit configured to display the object image; and an input unit configured to receive an input for displaying a marker indicating a direction of the object in the object image, before the X-ray source irradiates X-rays to photograph an X-ray image.

The controller determines whether the direction of the object indicated by the marker corresponds to information about an irradiation direction of X-rays, and if the direction of the object indicated by the marker does not correspond to the information about the irradiation direction of X-rays, the display unit outputs a warning.

The controller displays a marker indicating a direction of the object in an X-ray image based on the direction of the object indicated by the marker displayed in the object image.

The controller acquires object direction information from the object image, and if the direction of the object indicated by the marker does not correspond to the object direction information, the controller outputs a warning through the display unit.

In accordance with one aspect of the present disclosure, a method of controlling an X-ray imaging apparatus, includes photographing an object image; acquiring object direction information from the object image; determining whether the object direction information corresponds to information about an irradiation direction of X-rays; and if the object direction information does not correspond to the information about the irradiation direction of X-rays, outputting a warning.

The acquiring of the object direction information from the object image includes: recognizing the object from the object image; and acquiring the object direction information including at least one of an up direction, a down direction, a left direction, a right direction, a front direction, a rear direction, and a lateral direction of the object, based on a feature of the recognized object.

The method further includes: controlling an X-ray source to photograph an X-ray image; and displaying a marker indicating a direction of the object in the X-ray image based on the object direction information.

The method further includes: controlling an X-ray source to photograph an X-ray image; displaying the X-ray image;

and receiving an input for displaying a marker indicating a direction of the object in the X-ray image.

The method further includes, if the direction of the object indicated by the marker does not correspond to the object direction information, outputting a warning through a user interface.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Hereinafter, embodiments of an X-ray imaging apparatus and a control method thereof will be described in detail with reference to the accompanying drawings.

Figure 1:
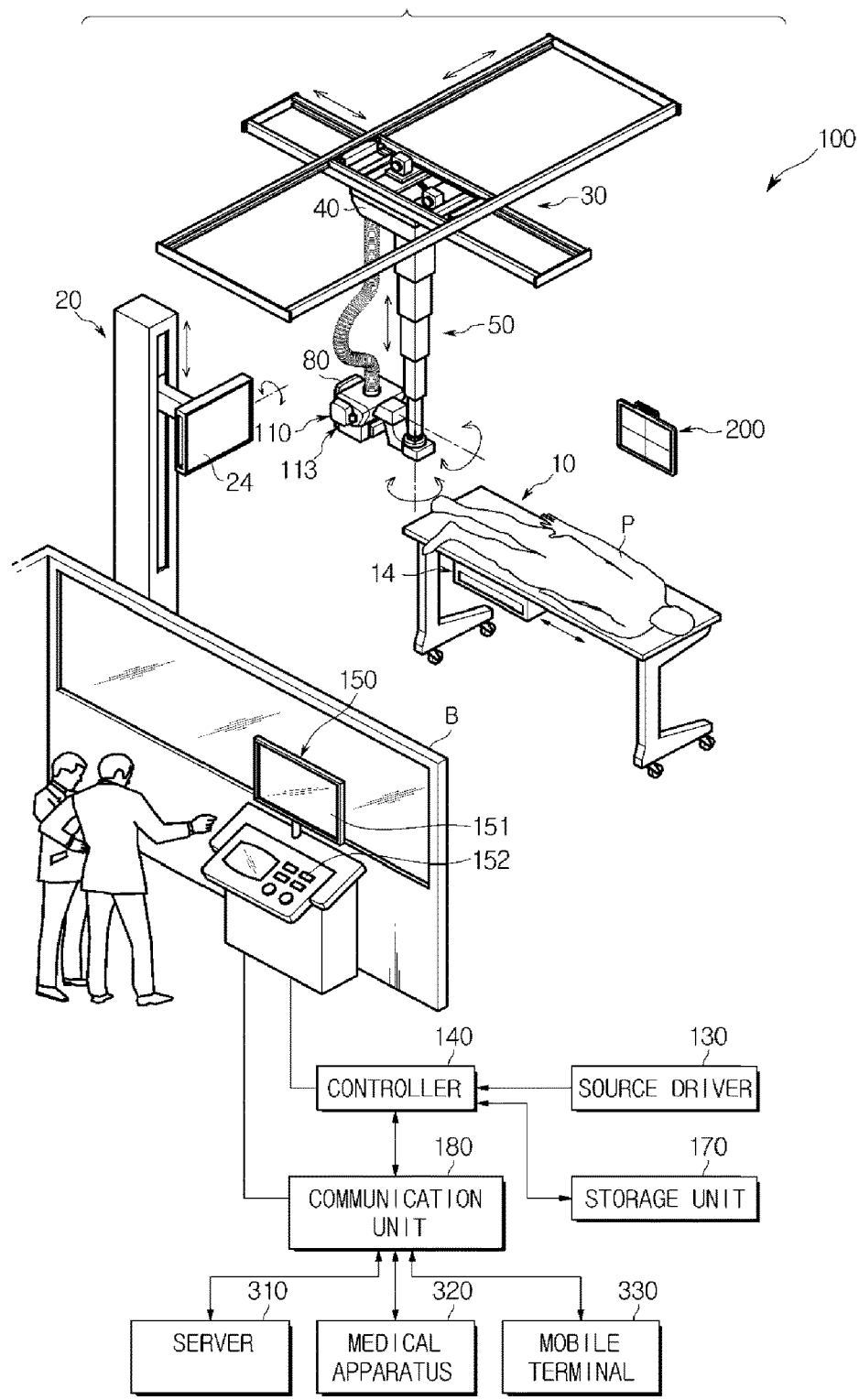
FIG. 1 shows a configuration of an X-ray imaging apparatus according to an embodiment of the present disclosure.

FIG. 1 shows a configuration of an X-ray imaging apparatus according to an embodiment of the present disclosure.

Referring to FIG. 1, an X-ray imaging apparatus 100 according to an embodiment of the present disclosure may include: an X-ray irradiator 110 configured to generate X-rays and to irradiate the X-rays onto an object; an imaging unit 120 (shown in FIG. 2), for example, an imaging device configured to photograph an object image; a source driver 130 configured to move the X-ray irradiator 110; a controller 140 configured to analyze the object image photographed by the imaging unit 120, and to acquire direction information of the object; a storage unit 170 configured to store an X-ray imaging protocol, the direction information of the object, X-ray images, etc.; and a communication unit 180 configured to communicate with an X-ray detector 200 or other external devices, and to transmit/receive data to/from the X-ray detector 200 or the other external devices. The object may be a patient.

Also, the X-ray imaging apparatus 100 may further include a user interface configured to provide a user with information, and to receive inputs from the user. The user interface may include a display unit 151 configured to display information about radiography, a screen for guiding a user to input control commands, an object image or an X-ray image photographed by the imaging unit 120, etc., and an input unit 152 configured to receive control commands from the user. Although not shown in FIG. 1, the user interface may include a speaker configured to output information via sound.

The X-ray irradiator 110 may include an X-ray source configured to generate X-rays, and a collimator configured to adjust an area onto which X-rays generated from the X-ray source are irradiated.

A guide rail 30 may be installed on the ceiling of a radiation room where the X-ray imaging apparatus 100 is installed. The X-ray irradiator 110 may be connected to a movement carriage 40 moving along the guide rail 30 to move the X-ray irradiator 110 to a location corresponding to an object P, wherein the X-ray irradiator 110 may be connected to the movement carriage 40 through a post frame 50 that can be folded so that the height of the X-ray irradiator 110 can be adjusted.

For example, the user interface may be provided in a workstation 150.

The input unit 152 may receive commands for an imaging protocol, scanning conditions, scanning timings, positioning of the X-ray irradiator 110, etc. The input unit 152 may include a keyboard, a mouse, a touch screen, a voice recognizer, etc.

The display unit 151 may display a screen for guiding a user's inputs, X-ray images, camera images, a screen displaying the status of the X-ray imaging apparatus 100, etc. The display unit 151 may be one of a Liquid Crystal Display (LCD), a Light Emitting Diode (LED) display, and an Organic Light Emitting Diode (OLED) display. Also, the display unit 151 may output medical images as two-dimensional (2D) images or three-dimensional (3D) images.

The controller 140 may control scanning timings, scanning conditions, etc. of the X-ray irradiator 110 according to a command received from a user, and may create a medical image based on image data received from the X-ray detector 200. Also, the controller 140 may control the location or position of an installation member 14 or 24 in which the X-ray irradiator 110 or the X-ray detector 200 is installed, according to the imaging protocol and the position of the object P.

The controller 140 may include a memory in which programs for performing the above-described operations and operations to be described later are stored, and a processor to execute the stored programs. The controller 140 may include a single processor, or a plurality of processors. If the controller 140 includes a plurality of processors, the plurality of processors may be integrated into a single chip, or physically separated from each other.

The X-ray imaging apparatus 100 may be connected to an external server 310, a medical apparatus 320, and a mobile terminal 330 through the communication unit 180 so as to transmit/receive data to/from the external server 310, the medical apparatus 320, and the mobile terminal 330. The communication unit 180 may be connected to the external server 310 to transmit/receive data related to diagnosis of an object. For example, the communication unit 180 may receive information about a patient's diagnosis history, therapeutic schedule, etc. from the external server 310 and use the information for diagnosis of an object. Also, the communication unit 180 may transmit image data acquired by the X-ray imaging apparatus 100 to the external server 310. For example, the external server 310 may be Picture Archiving Communication System (PACS).

Also, the communication unit 180 may receive image data acquired by another X-ray imaging apparatus or the medical apparatus 320 of another modality, such as a Computerized Tomography (CT) apparatus, a Magnetic Resonance Imaging (MRI) apparatus, an ultrasonic imaging apparatus, etc., or may transmit image data acquired by the X-ray imaging apparatus 100.

Also, the communication unit 180 may communicate with a user's or patient's mobile terminal 330, such as a mobile phone, Personal Digital Assistant (PDA), a laptop computer, etc. For example, the communication unit 180 may transmit information related to diagnosis of an object or image data acquired by the X-ray imaging apparatus 100 to the mobile terminal 330.

Also, the communication unit 180 may receive a control signal from the mobile terminal 330, and transfer the received control signal to the controller 140 so as to enable the controller 140 to control the X-ray imaging apparatus 100 according to the received control signal. In this case, a program for controlling the X-ray imaging apparatus 100 may be installed in the mobile terminal 330. The program may include commands for performing the entire or a part of operations of the controller 140. The program may have been installed in advance in the mobile terminal 330, or may be downloaded and installed by a user of the mobile terminal 330 from a server providing the related application. The server providing the application may include recording medium in which the corresponding program is stored.

The communication unit 180 may include at least one component for enabling communications with external devices. For example, the communication unit 180 may include at least one of a short-range communication module, a wired communication module, and a wireless communication module.

Meanwhile, the X-ray detector 200 may be implemented as a fixed type X-ray detector fixed at a stand 20 or a table 10, or as a portable X-ray detector that can be detachably attached at the installation member 14 or 24 or used at an arbitrary location. The portable X-ray detector may be implemented as a wired type or a wireless type according to a data transfer method and a power supply method.

The X-ray detector 200 may be included or not included as a component of the X-ray imaging apparatus 100. If the X-ray detector 200 is included as a component of the X-ray imaging apparatus 100, the X-ray detector 200 may be connected to the controller 120 through an internal communication module of the X-ray imaging apparatus 100 to receive control signals from the controller 120 or to transmit image data to the controller 120. If the X-ray detector 200 is not included as a component of the X-ray imaging apparatus 100, the X-ray detector 200 may be connected to the X-ray imaging apparatus 100 through the communication unit 140.

On one side of the X-ray detector 200, a sub user interface 80 may be mounted to provide the user with information and to receive commands from the user. The sub user interface 80 may perform the entire or a part of functions that the input unit 152 and the display unit 151 of the workstation 150 perform.

In FIG. 1, a fixed type X-ray imaging apparatus connected to the ceiling of the radiation room is shown, however, the X-ray imaging apparatus 100 may be any one of various kinds of X-ray imaging apparatuses, such as a C-arm type X-ray imaging apparatus and a mobile X-ray imaging apparatus, which are well-known to one of ordinary art in the art.

Figure 2:
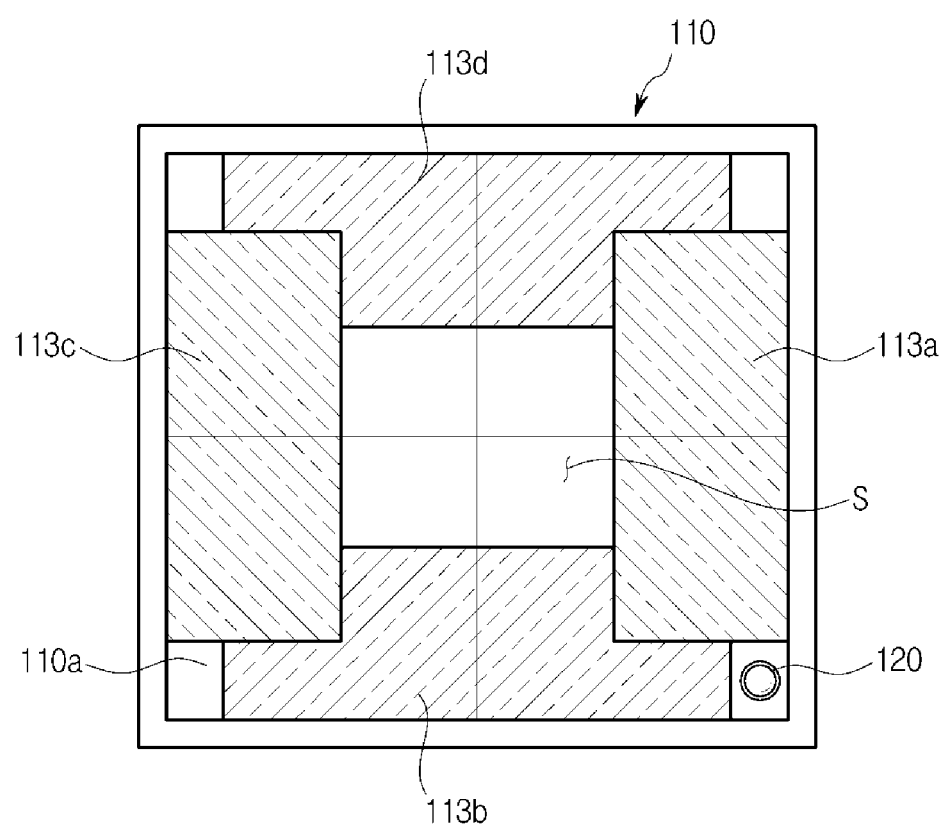
FIG. 2 shows an X-ray source seen in a direction in which X-rays are irradiated.

FIG. 2 shows an X-ray source seen in a direction in which X-rays are irradiated.

As described above, the X-ray irradiator 110 may include an X-ray tube to generate X-rays, and the collimator to adjust an irradiation area of the generated X-rays. The collimator may be located in front of the X-ray tube, that is, in the direction in which X-rays are irradiated.

Referring to FIG. 2, a collimator 113 may include a plurality of blades 113a, 113b, 113c, and 113d that are movable and absorb X-rays. X-rays may be irradiated through a slot S formed by the plurality of blades 113a, 113b, 113c, and 113d.

Meanwhile, the imaging unit 120 may be installed adjacent to the collimator 113. The X-ray irradiator 110 may photograph an X-ray image of an object, and the imaging unit 120 may be implemented as a camera, such as a Charge Coupled Device (CCD) camera or a Complementary Metal-Oxide Semiconductor (CMOS) camera, to photograph still images or moving images. The still images may be photographed periodically, or captured at specific times when a moving image is photographed. For example, by capturing a still image at a specific time when photographing a moving image, an object image can be acquired. In the current embodiment, in order to distinguish an image photographed by the camera from an X-ray image, an image photographed by the camera will be referred to as an object image.

If a predetermined event occurs, the controller 140 may control the imaging unit 120 to capture a still image. The event for capturing the still image may be a user's control command input through an input unit provided in a device, such as the workstation 150 or the sub user interface 80.

An object image may be captured when the control command is input, when a predetermined time elapses after the control command is input, or periodically for a predetermined time period after the control command is input.

Also, the controller 140 may analyze a moving image photographed by the imaging unit 120 in real time to detect motion, and if no motion is detected for a predetermined time period, the controller 140 may determine that the imaging unit 120 is ready for radiography, and capture an object image.

The control command may be a command for capturing an object image or a command for irradiating X-rays. If the control command is a command for irradiating X-rays, an object image may be photographed after the control command is input, and then X-rays may be irradiated.

The imaging unit 120 may be, as shown in FIG. 2, positioned in the same direction in which the X-ray irradiator 110 irradiates X-rays. That is, the imaging unit 120 may be positioned such that it can photograph an object in a direction in which the object is located.

However, the case in which the imaging unit 120 is installed in the X-ray irradiator 110 is only an example, and the imaging unit 120 may be provided at another location instead of the X-ray irradiator 110. If the imaging unit 120 is installed in the X-ray irradiator 110, an offset between an area appearing in an X-ray image and an area appearing in an object image may be reduced so that a user can easily perform a setting related to the X-ray image while seeing the object image.

FIGS. 3A, 3B, 3C, and 3D are views for comparing object images photographed by an imaging unit to the corresponding X-ray images. In the current embodiment, the object may be a human body.

An X-ray image may be photographed according to one of various X-ray imaging protocols, wherein the X-ray imaging protocol may include information about a photographing part of an object and information about an irradiation direction of X-rays. The photographing part may be one of various body parts, such as the head (skull), the neck, the chest, the arm, the hand, the waist, the leg, etc., and the irradiation direction of X-rays may be one of AnteroPosterior (AP), PosteroAnterior (PA), and Lateral (LAT).

Figure 3A:
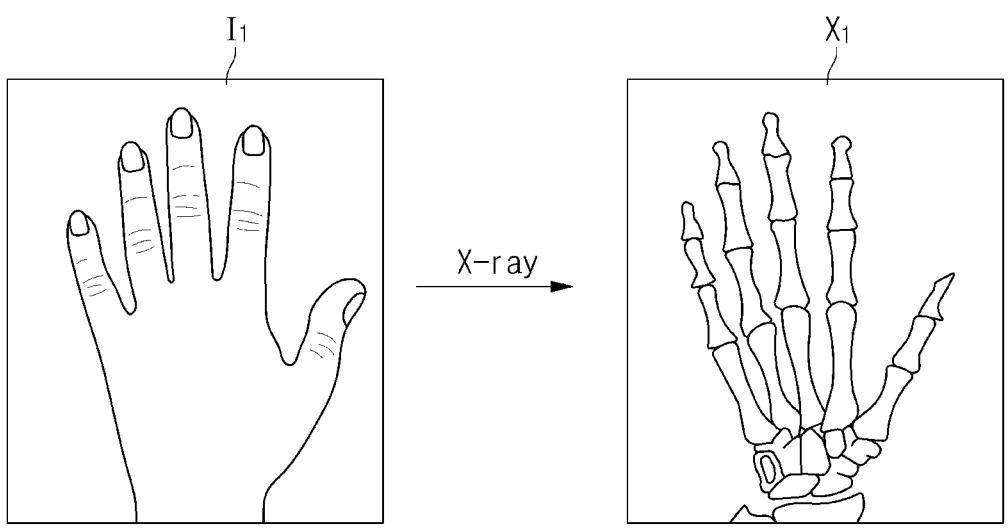
FIGS. 3A, 3B, 3C, and 3D are views for comparing object images photographed by an imaging unit to the corresponding X-ray images.
Figure 3B:
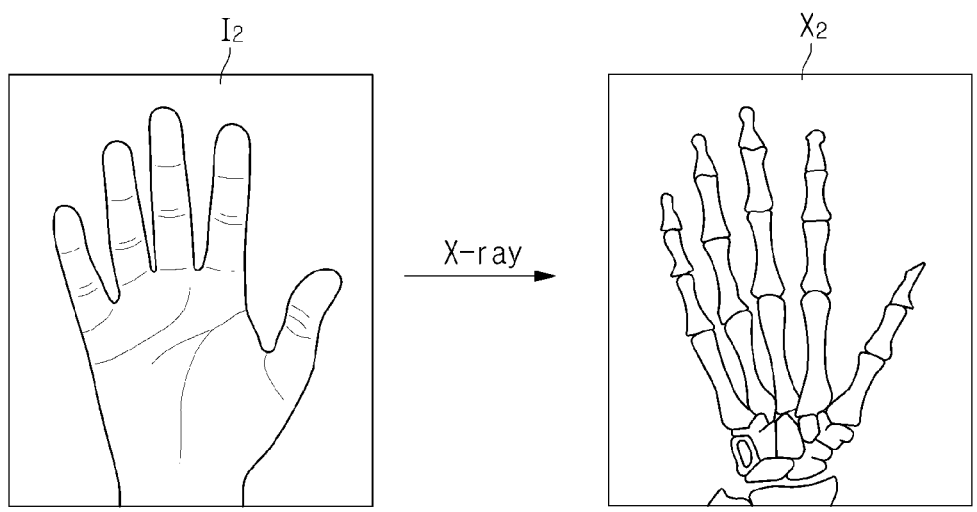

As shown in FIGS. 3A and 3B, if a left hand PA X-ray image $X_1$ acquired by irradiating X-rays on the left hand of an object in a PA direction is compared to a right hand AP X-ray image $X_2$ acquired by irradiating X-rays on the right hand of the object in an AP direction, it is difficult to distinguish between the right hand AP X-ray image $X_2$ and the left hand PA X-ray image $X_1$. The reason is because X-ray images include no information about the front-back positions of materials constituting an object in a direction in which X-rays are irradiated, although including other information about the materials of the object through which the X-rays are transmitted.

However, if a left hand PA object image $I_1$ acquired by photographing the front side of the left hand through the imaging unit 120 is compared to a right hand AP object image $I_2$ acquired by photographing the rear side of the right hand through the imaging unit 120, it is possible to correctly distinguish between the left hand PA and the right hand AP based on optically distinguishing features, such as the existence/absence of the nails, the lengths of the fingers, the lines of the palms, etc.

Figure 3C:
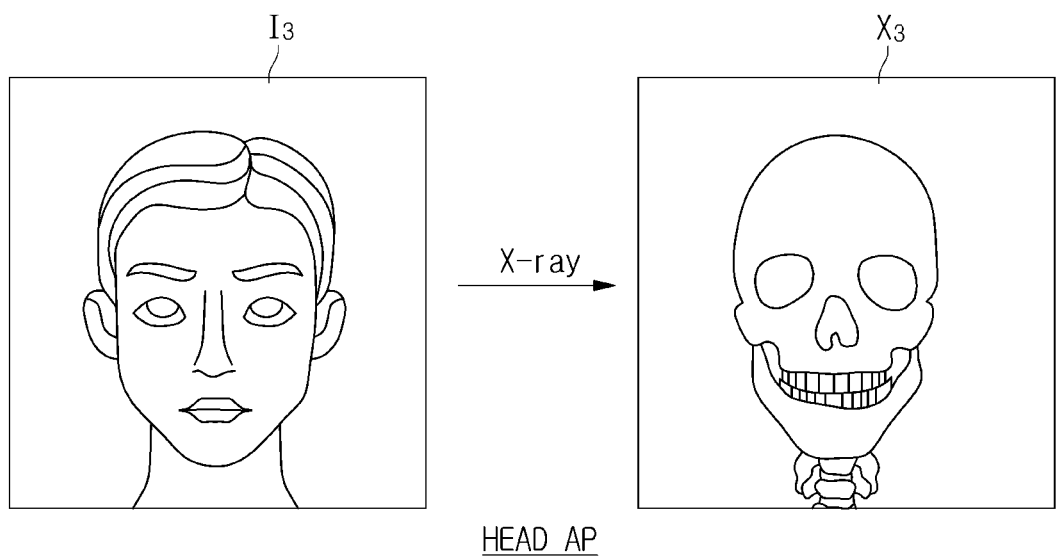
Figure 3D:
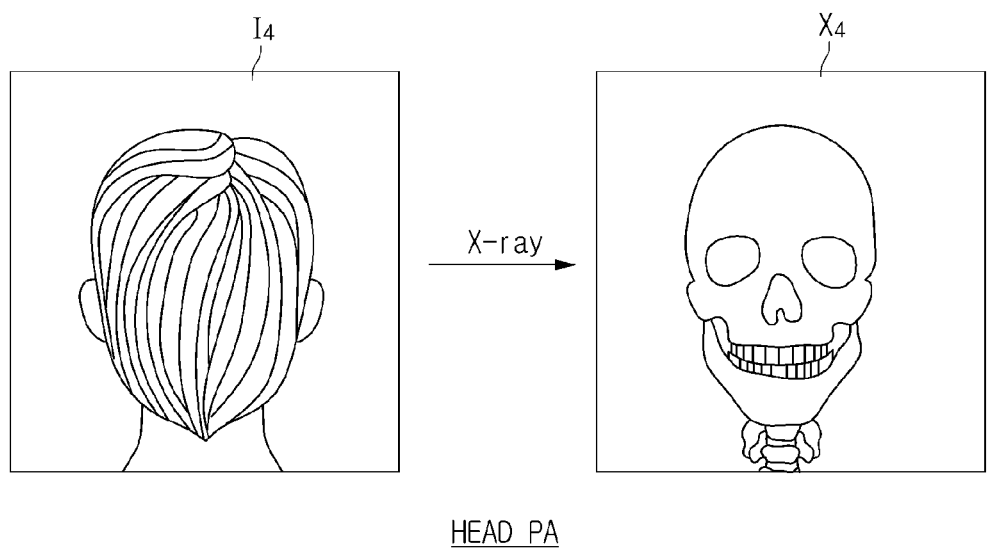

Also, as shown in FIGS. 3C and 3D, if a head AP X-ray image $X_3$ acquired by irradiating X-rays onto the head of an object in the AP direction is compared to a head PA X-ray image $X_4$ acquired by irradiating X-rays onto the head of the object in the PA direction, it is difficult to distinguish between the head PA X-ray image $X_4$ and the head AP X-ray image $X_3$.

However, if a head AP object image $I_3$ acquired by photographing the front side of the head through the imaging unit 120 is compared to a head PA object image $I_4$ acquired by photographing the rear part of the head through the imaging unit 120, it is possible to correctly distinguish between the head AP and the head PA based on optically distinguishing features, such as the eyes, nose, and lips appearing on the face of the object.

Accordingly, the X-ray imaging apparatus 100 according to an embodiment of the present disclosure can determine direction information of an object appearing on an X-ray image based on an object image photographed by the imaging unit 120. Hereinafter, an embodiment will be described in detail.

Figure 4:
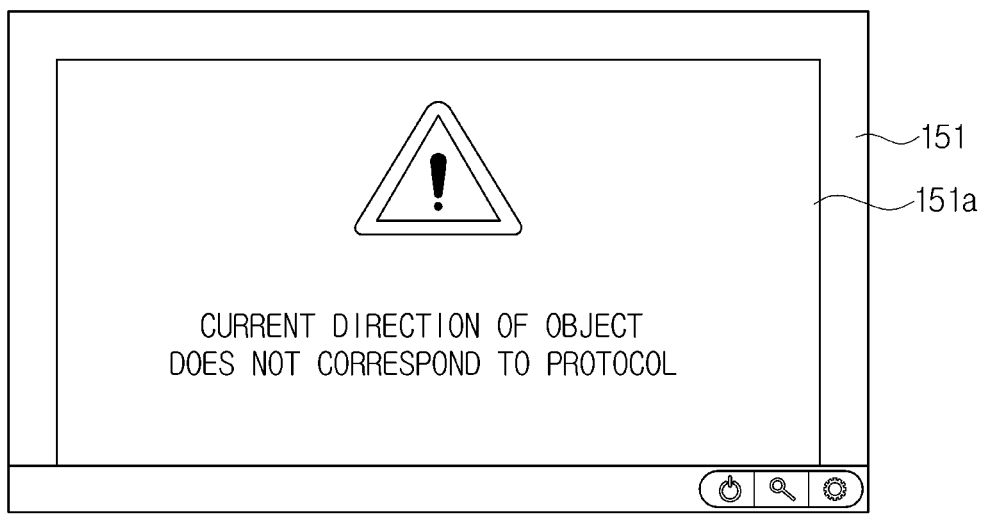
FIG. 4 shows an example of a warning screen output through a display unit.

FIG. 4 shows an example of a warning screen output through a display unit.

For radiography, a user may select an X-ray imaging protocol. As described above, information about X-ray imaging protocols may be stored in the storage unit 170, and the user may select a desired X-ray imaging protocol through the input unit 152.

Then, the user may align the position and location of an object and the locations of the X-ray irradiator 110 and the X-ray detector 200, according to the selected X-ray imaging protocol.

For example, if the selected X-ray imaging protocol relates to the head AP of the object, the user may align the object such that the object stands with the back of his/her head toward the X-ray detector 200 and faces the X-ray irradiator 110.

The imaging unit 120 may photograph a moving image in real time, and display the photographed moving image on the display unit 151. However, the X-ray imaging apparatus 100 is not limited to the current embodiment, and a camera for photographing the moving image may be separated from the imaging unit 120.

If a predetermined event occurs to photograph an object image, the imaging unit 120 may capture a still image, and the captured still image may be used as an object image. For example, an object image may be photographed at at least one time before X-rays are irradiated after the position and location of the object are aligned for radiography.

The controller 140 may acquire object direction information from the object image using one of various recognition algorithms. The object direction information may include information indicating an up, down, left, or right direction with respect to the object, and information indicating the front part, rear part, or lateral part of the object.

For example, the controller 140 may perform boundary detection to recognize a photographed part of the object, that is, the head, the chest, the hand, etc. appearing on the object image, to recognize features of the eyes, nose, lips, etc. appearing on the face, and to recognize features of the nails, lines, etc. appearing on the hand.

The controller 140 may acquire the object direction information based on the features. Referring again to FIGS. 3A and 3B, the controller 140 may recognize nails appearing on the left hand PA object image $I_1$ to determine that the corresponding image $I_1$ relates to a hand's front side, and recognize the lengths and arrangement of the fingers to determine that the corresponding image $I_1$ relates to a left hand.

Also, the controller 140 may recognize that no nail exists in the right hand AP object image $I_2$ to determine that the corresponding image $I_2$ is a hand's rear side, and recognize the lengths and arrangement of the fingers to determine that the corresponding image $I_2$ relates to a right hand.

Referring again to FIGS. 3C and 3D, the controller 140 may recognize eyes, nose, and lips from the head AP object image $I_3$ to determine that the corresponding image $I_3$ relates to a head's front side, and to determine that the left part of the image $I_3$ is the right part of the object and the right part of the image $I_3$ is the left part of the object.

Also, the controller 140 may recognize that none of eyes, nose, and lips exists in the head PA object image $I_4$ to determine that the image $I_4$ relates to the rear part of the object, and determine that the left part of the image $I_4$ is the left part of the object and the right part of the image $I_4$ is the right part of the object.

The controller 140 may determine whether information about a photographing part and information about an irradiation direction of X-rays, included in the selected X-ray imaging protocol correspond to information about a photographing part of an object and direction information of the object appearing on the object image.

For example, if the selected X-ray imaging protocol relates to head AP, and an object image photographed by the imaging unit 120 is the head PA object image $I_4$ of FIGS. 3C and 3D as described above, the controller 140 may determine that object direction information is the rear part of the object, and corresponds to the PA direction, based on the object image.

That is, if the selected X-ray imaging protocol relates to the AP direction, but object direction information acquired from an object image corresponds to the PA direction, the controller 140 may control the display unit 151 to display a warning screen 151a notifying that the current direction of the object does not correspond to the protocol, as shown in FIG. 4. However, the method of outputting a warning visually is only an example, and a warning may be audibly output through a speaker provided in the X-ray imaging apparatus 100.

If a user realigns the location or position of the object after the warning is output, the imaging unit 120 may again photograph an object image, and the controller 140 may repeat the above-described operations.

If the information about the irradiation direction of X-rays of the selected X-ray imaging protocol matches with the object direction information acquired from the object image, that is, if the object direction information corresponds to the selected X-ray imaging protocol, radiography can be directly performed without outputting any warning.

Then, the X-ray irradiator 110 may irradiate X-rays onto the object, and the X-ray detector 200 may detect X-rays transmitted through the object, convert the detected X-rays into an electrical signal, and then transfer the electrical signal to the controller 140 through the communication unit 180. The electrical signal transferred from the X-ray detector 200 may be an X-ray image.

Figure 5:
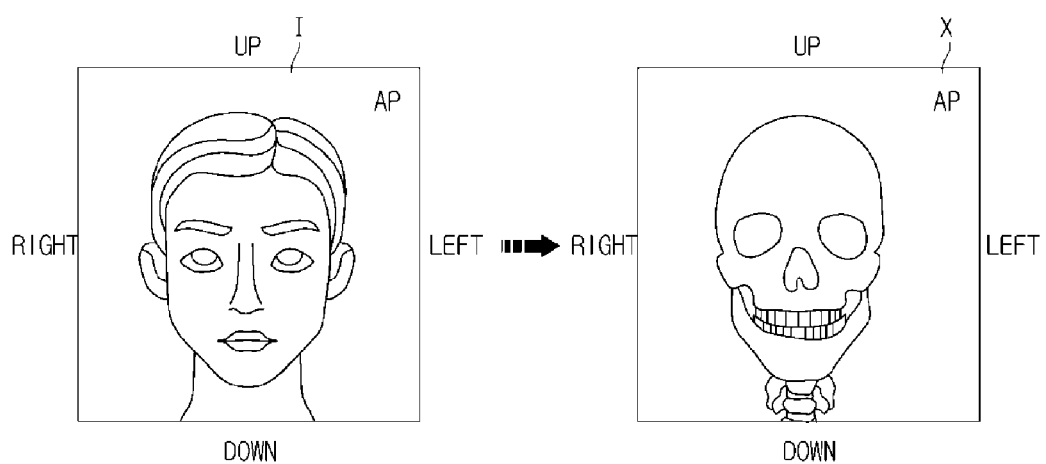
FIG. 5 shows an example of information that is stored together with an X-ray image.
Figure 6:
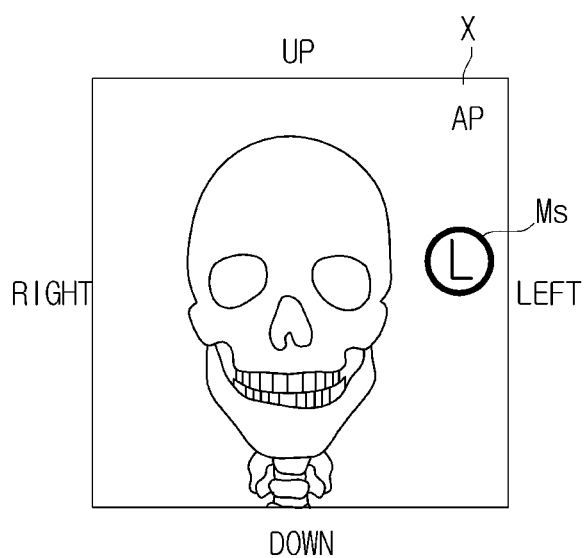
FIG. 6 shows an example of a marker displayed in an X-ray image.
Figure 7:
FIG. 7 shows an example of a warning screen that is output when a wrong marker is displayed.

FIG. 5 shows an example of information that is stored together with an X-ray image, FIG. 6 shows an example of a marker displayed in an X-ray image, and FIG. 7 shows an example of a warning screen that is output when a wrong marker is displayed.

The controller 140 may store object direction information acquired from an object image, together with the corresponding X-ray image, in the storage unit 170. Referring to the example of FIG. 5, if the controller 140 determines that the left part of an object image I is the right part of the object, the right part of the object image I is the left part of the object, the upper part of the object image I is the upper part of the object, and the lower part of the object image I is the lower part of the object, the controller 140 may correspond the object direction information to an X-ray image X, and store the object direction information together with the X-ray image X. Based on the object direction information corresponding to the X-ray image X, the up, down, left, and right directions of the object in the X-ray image X, and whether the corresponding X-ray image X is an AP image or a PA image can be determined.

Meanwhile, the controller 140 may automatically display a marker Ms indicating a direction of the object in the X-ray image X, based on the object direction information stored together with the X-ray image X, as shown in FIG. 6. The X-ray image including the marker Ms may be stored in the storage unit 170, or transferred to another device through the communication unit 180. For example, the X-ray image X may be transferred to PACS or to another computer or a mobile device registered in advance, through the communication unit 180. If the marker Ms is displayed in the X-ray image X, a person who examines the X-ray image X to perform diagnosis can easily check the direction of the object to make an accurate diagnosis.

Alternatively, the user may himself/herself add a marker Ms in the X-ray image X. In this case, the X-ray image X may be displayed on the display unit 151, and the input unit 152 may receive a user's input regarding the kind and location of a marker. The user's input may be operation of dragging an icon corresponding to a marker to a desired location, or operation of inputting information about the kind, location, size, etc. of a marker. Herein, the kind of the marker may depend on the direction of the marker. For example, the kind of the marker may include a left marker, a right marker, an up marker, a down marker, a front marker, a rear marker, a lateral marker, etc.

The controller 140 may determine whether the direction of the object indicated by the marker corresponds to the object direction information, and if the controller 140 determines that the direction of the object does not correspond to the object direction information, the controller 140 may output a warning through a user interface.

For example, if the right marker is displayed to the left of an object, the controller 140 may control the display unit 151 to display a warning screen 151b notifying that input marker information does not correspond to object direction information, as shown in FIG. 7. Also, the controller 140 may output an aural warning through the speaker.

Figure 8:
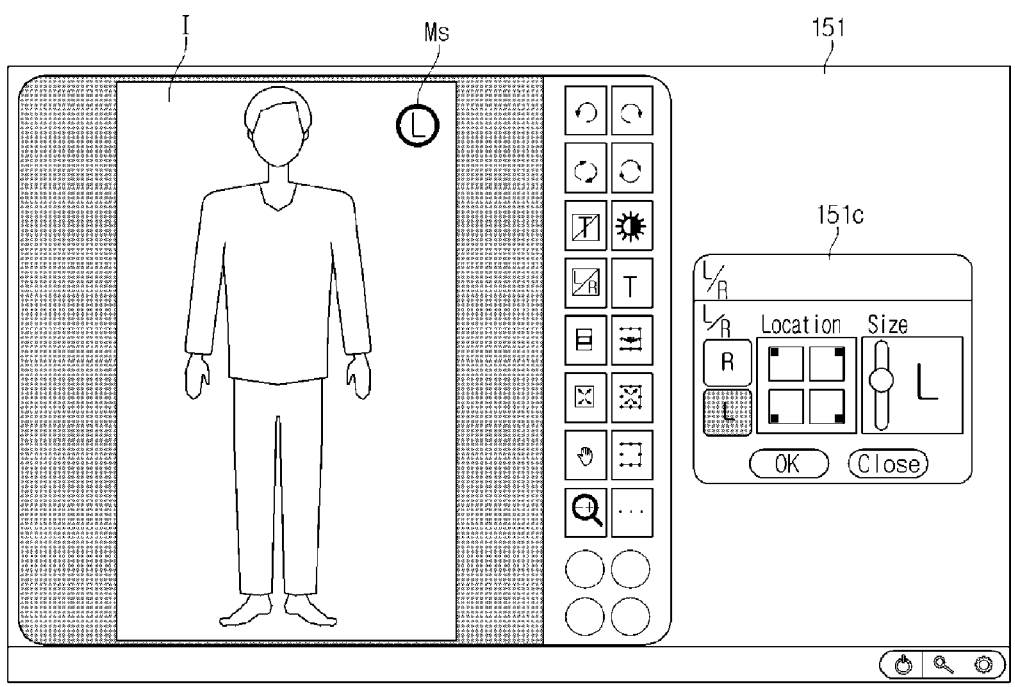
FIG. 8 shows an example of a screen for receiving marker information from a user by displaying an object image before radiography.
Figure 9:
FIG. 9 shows an example of a warning screen output when input marker information does not correspond to a selected X-ray imaging protocol.

FIG. 8 shows an example of a screen for receiving marker information from a user by displaying an object image before radiography, and FIG. 9 shows an example of a warning screen output when input marker information does not correspond to a selected X-ray imaging protocol.

In the above-described example, a case of photographing an X-ray image and then displaying a marker in the X-ray image has been described. According to another example, as shown in FIG. 8, an object image I may be displayed on the display unit 151 before an X-ray image is photographed, and a marker display tool 151c for displaying a marker Ms indicating the direction of the object may be displayed on the display unit 151, together with the object image I. Since the object image I enables a user to easily determine the direction of the object unlike an X-ray image, the user can add a marker with higher accuracy than the case of adding a marker in an X-ray image.

The user may input information about the kind, location, and size of the marker Ms through the input unit 152. If the user inputs the marker information, the marker Ms can be displayed in the object image I according to the input marker information.

Meanwhile, the kind and location of the marker Ms may represent the direction of the object. The controller 140 may compare information about an irradiation direction of X-rays included in a selected X-ray imaging protocol to the direction of the object indicated by the marker Ms. If the controller 140 determines that the information about the irradiation direction of X-rays does not correspond to the direction of the object, the controller 140 may control the display unit 151 to display a warning screen 151d notifying that the input marker information does not correspond to the irradiation direction of X-rays of the protocol, as shown in FIG. 9.

For example, as shown in FIG. 8, if a left marker Ms indicating the left part of an object is displayed in the right part of the object image I, this means a state in which the front side of the object faces the X-ray irradiator 110. However, if a selected X-ray imaging protocol relates to chest PA, it can be determined that the direction of the object is misaligned, and accordingly, a warning may be output in order for a user to realign the object.

Figure 10:
FIG. 10 shows an example of a warning screen output when input marker information does not correspond to object direction information.

FIG. 10 shows an example of a warning screen 151e output when input marker information does not correspond to object direction information.

In the above-described example, the controller 140 may compare the direction of an object indicated by an input marker to information about an irradiation direction of X-rays of a selected X-ray imaging protocol, under the assumption that marker information input by a user is correct. According to another example, the controller 140 may acquire object direction information from an object image I, and determine whether marker information input by a user is correct, based on the acquired object direction information.

If the controller 140 determines that the direction of the object indicated by the marker does not correspond to the object direction information determined based on the object image I, the controller 140 may control the display unit 151 to display a warning screen as shown in FIG. 10, thereby notifying that wrong marker information was input.

Figure 11:
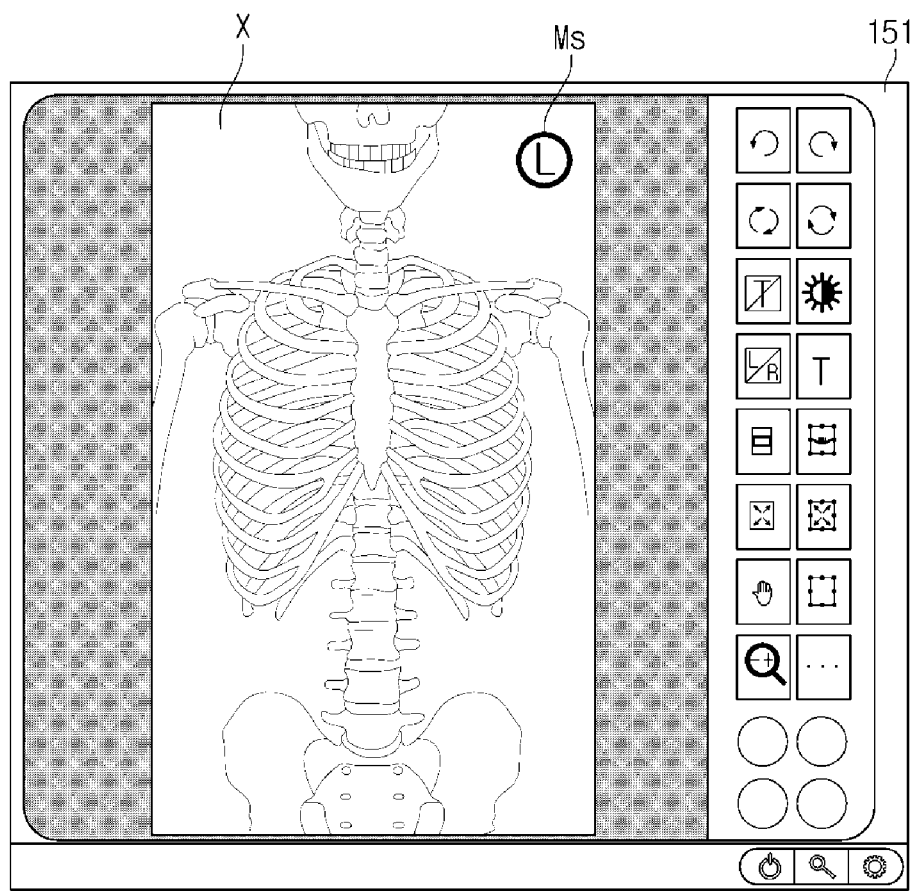
FIG. 11 is a view for describing an example in which a marker is automatically displayed in an X-ray image.

FIG. 11 is a view for describing an example in which a marker is automatically displayed in an X-ray image.

A marker added by a user before radiography according to the above-described examples may be automatically displayed in an X-ray image, as shown in FIG. 11. More specifically, the controller 140 may display a marker Ms indicating the direction of an object in an X-ray image, based on marker information input by a user before radiography and a selected X-ray imaging protocol. Accordingly, a process in which a user adds a marker after radiography can be omitted, and an error which may be generated when a user adds a marker while seeing an X-ray image from which he/she cannot easily determine the direction of an object can be prevented.

Figure 12:
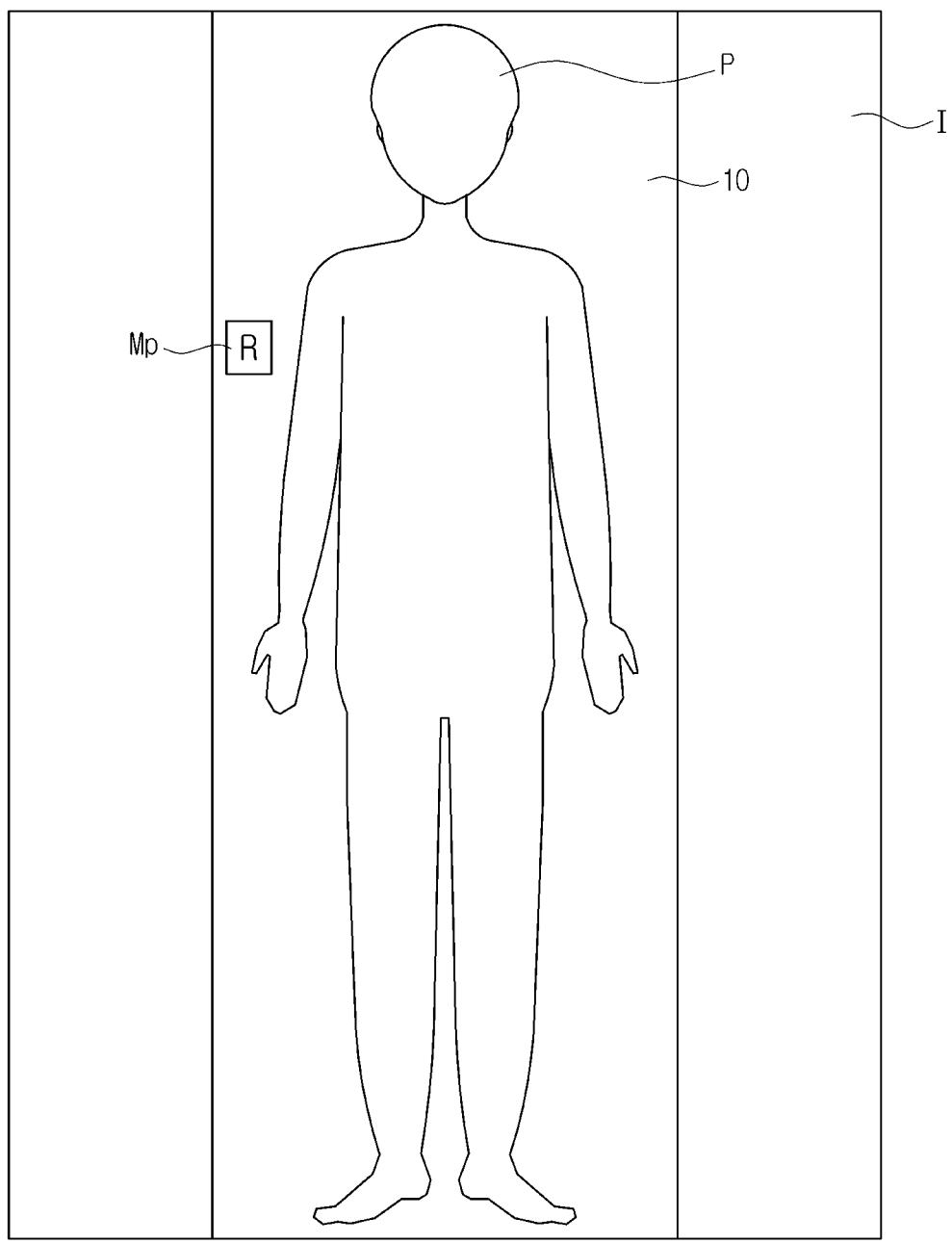
FIG. 12 is a view for describing an example of recognizing a hardware marker.

FIG. 12 is a view for describing an example of recognizing a hardware marker.

In the above-described examples, the marker added in the object image or the X-ray image by the user may be a kind of a software marker. However, according to another example, it is also possible to photograph an object image or an X-ray image after locating a hardware marker adjacent to the real object. Referring to the example of FIG. 12, when an object P lies on a radiography table 10, a user may locate a hardware marker Mp made of a material (for example, lead (Pb)) that can appear on an X-ray image, on the radiography table 10, in correspondence to the direction of the object P. In the current example, the user may locate a right marker Mp indicating a right direction to the right of the object P.

The imaging unit 120 may photograph an object image I, and the controller 140 may recognize the hardware marker Mp from the object image I. For this, features (for example, shape, color, pattern, etc.) of the hardware marker Mp may be stored in advance in the storage unit 170.

The controller 140 may recognize the hardware marker Mp, and also recognize a relative position of the hardware marker Mp with respect to the object P. For example, the controller 140 may recognize which side of the object P the marker Mp indicating the right direction is located to.

The recognized marker information may include the direction of the object. The kind and location of the hardware marker Mp may represent the direction of the object. The controller 140 may compare the recognized marker information to information about an irradiation direction of X-rays included in a selected X-ray imaging protocol, and determine whether the recognized marker information corresponds to the information about the irradiation direction of X-rays. If the controller 140 determines that the recognized marker information does not correspond to the information about the irradiation direction of X-rays, the controller 140 may control the display unit 151 to display a warning screen notifying that the recognized marker information does not correspond to the information about the irradiation direction of X-rays.

Also, as shown in FIG. 11, a software marker Ms may be automatically displayed in an X-ray image X, according to the recognized information of the hardware marker Mp. More specifically, the controller 140 may display a software marker Ms in an X-ray image X, according to the position of the hardware marker Mp in the object image I and the direction of the object indicated by the hardware marker Mp.

The X-ray image X in which the marker Ms is displayed may be stored in the storage unit 170, or transferred to another external device such as PACS through the communication unit 170.

The controller 140 which performs the above-described operations may include a memory in which a program for performing the operations is stored, and a processor for executing the stored program. Also, the memory may temporarily or non-temporarily store data output when the program is executed, or data required for executing the program.

The processor constituting the controller 140 may be implemented as a single processor, as a plurality of processors integrated into a single chip, or as a plurality of physically separated processors.

The memory constituting the controller 140 may be separated from the memory constituting the storage unit 170, or may be shared with the storage unit 170. Also, the memory may include a volatile memory to temporarily store data, and a non-volatile memory to non-temporarily store data.

Also, the controller 140 may be installed in the workstation 150, in the sub user interface 80, or in an external mobile device. Alternatively, the processor or the memory constituting the controller 140 may be physically distributed so that a part of the functions of the controller 140 can be performed by the workstation 150, and another part of the functions of the controller 140 can be performed by the sub user interface 80. That is, the number or physical locations of processors constituting the controller 140 are not limited.

Meanwhile, if the controller 140 is installed in an external mobile device, such as a smart phone, a smart watch, smart glasses, or a tablet PC, a program for performing the entire or a part of the above-described operations of the controller 140 may be installed in the mobile device.

The program may be stored in recording medium included in the mobile device when the mobile device is released, or the program may be downloaded and installed from an external server providing the related application by a user of the mobile device. In the latter case, the corresponding program may be stored in recording medium installed in the external server providing the related application.

The recording medium, which is computer-readable recording medium, may be magnetic recording medium (for example, Read Only Memory (ROM), a floppy disc, a hard disc, etc.) or optical recording medium (for example, Compact Disc-Read Only Memory (CD-ROM), Digital Video Disc (DVD), etc.). However, the recording medium is not limited to the above-mentioned examples.

Hereinafter, a method of controlling an X-ray imaging apparatus, according to an embodiment of the present disclosure, will be described. The X-ray imaging apparatus may be the X-ray imaging apparatus 100 as described above.

Accordingly, the above description with reference to FIGS. 1 to 12 can be applied to the method of controlling the X-ray imaging apparatus.

Figure 13:
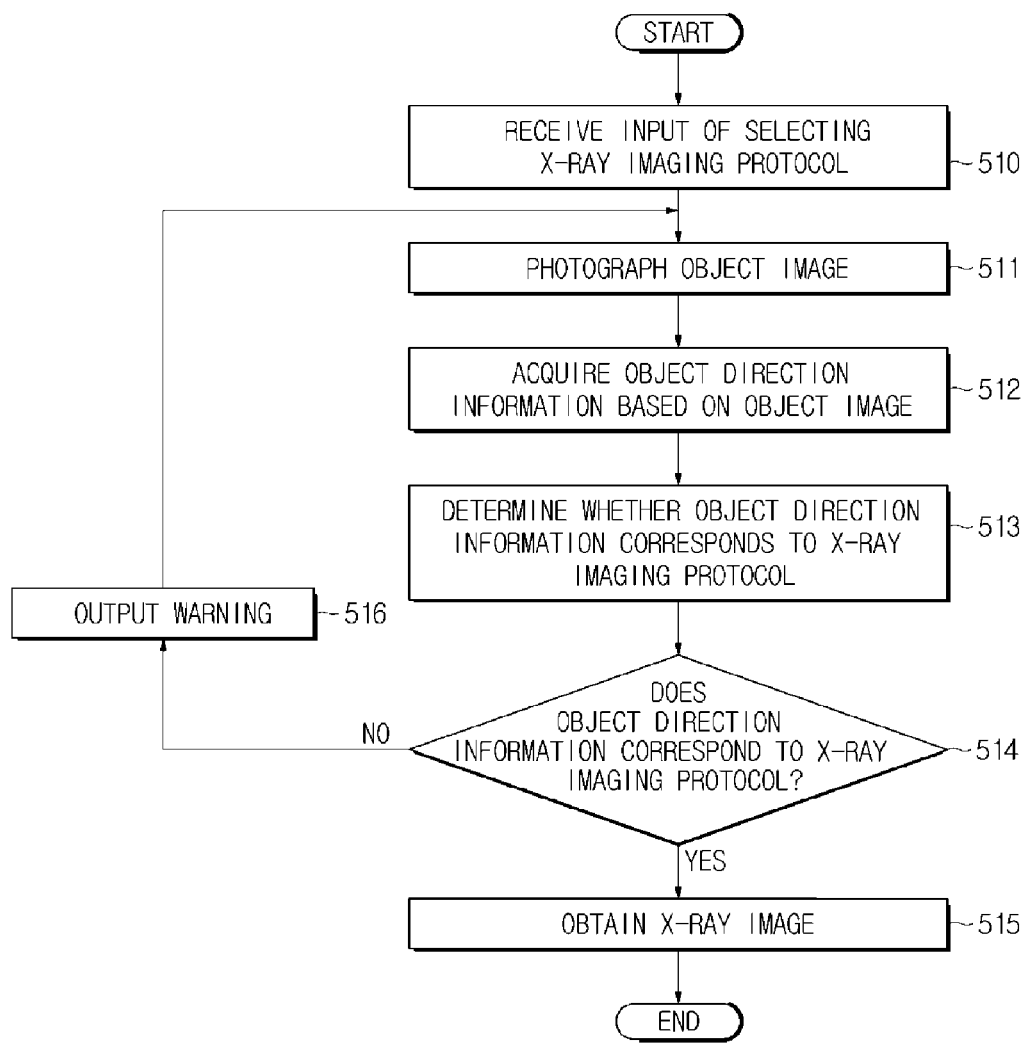
FIG. 13 is a flowchart illustrating a method of controlling an X-ray imaging apparatus, according to an embodiment of the present disclosure.

FIG. 13 is a flowchart illustrating a method of controlling an X-ray imaging apparatus, according to an embodiment of the present disclosure.

Referring to FIG. 13, an input of selecting an X-ray imaging protocol may be received from a user, in operation 510. The X-ray imaging protocol may include information about a photographing part of an object and information about an irradiation direction of X-rays. The user may select a desired X-ray imaging protocol through the input unit 152.

Then, an object image may be photographed, in operation 511. The object image may be photographed by the imaging unit 120, and the object image may be a still image captured when a specific event occurs. The specific event may be a control command input by the user. Alternatively, the controller 140 may analyze a moving image photographed by the imaging unit 120 in real time to detect motion, and if no motion is detected for a predetermined time period, the controller 140 may determine that the imaging unit 120 is ready for radiography, and capture an object image.

Then, object direction information may be acquired from the object image, in operation 512. The controller 140 may acquire the object direction information from the object image, using one of various recognition algorithms. The object direction information may include information indicating an up, down, left, or right direction with respect to the object, and information indicating the front part, rear part, or lateral part of the object.

Then, it may be determined whether the object direction information corresponds to the X-ray imaging protocol, in operation 513. The controller 140 may determine whether the information about the irradiation direction of X-rays included in the selected X-ray imaging protocol corresponds to the object direction information acquired from the object image, in operation 514. For example, if the selected X-ray imaging protocol relates to head AP, but the object direction information indicates the rear part of the object, the controller 140 may determine that the object direction information does not correspond to the X-ray imaging protocol.

If the object direction information does not correspond to the X-ray imaging protocol ("No" in operation 514), a warning may be output for the user, in operation 516, and if the position or location of the object is realigned, an object image may be again photographed, in operation 511. The warning may be a visual warning or an aural warning. That is, a method of outputting a warning is not limited as long as the warning can provide information notifying that object direction information does not correspond to a selected X-ray imaging protocol.

If the object direction information corresponds to the X-ray imaging protocol ("Yes" in operation 514), X-rays may be irradiated to capture an X-ray image, in operation 515.

Figure 14:
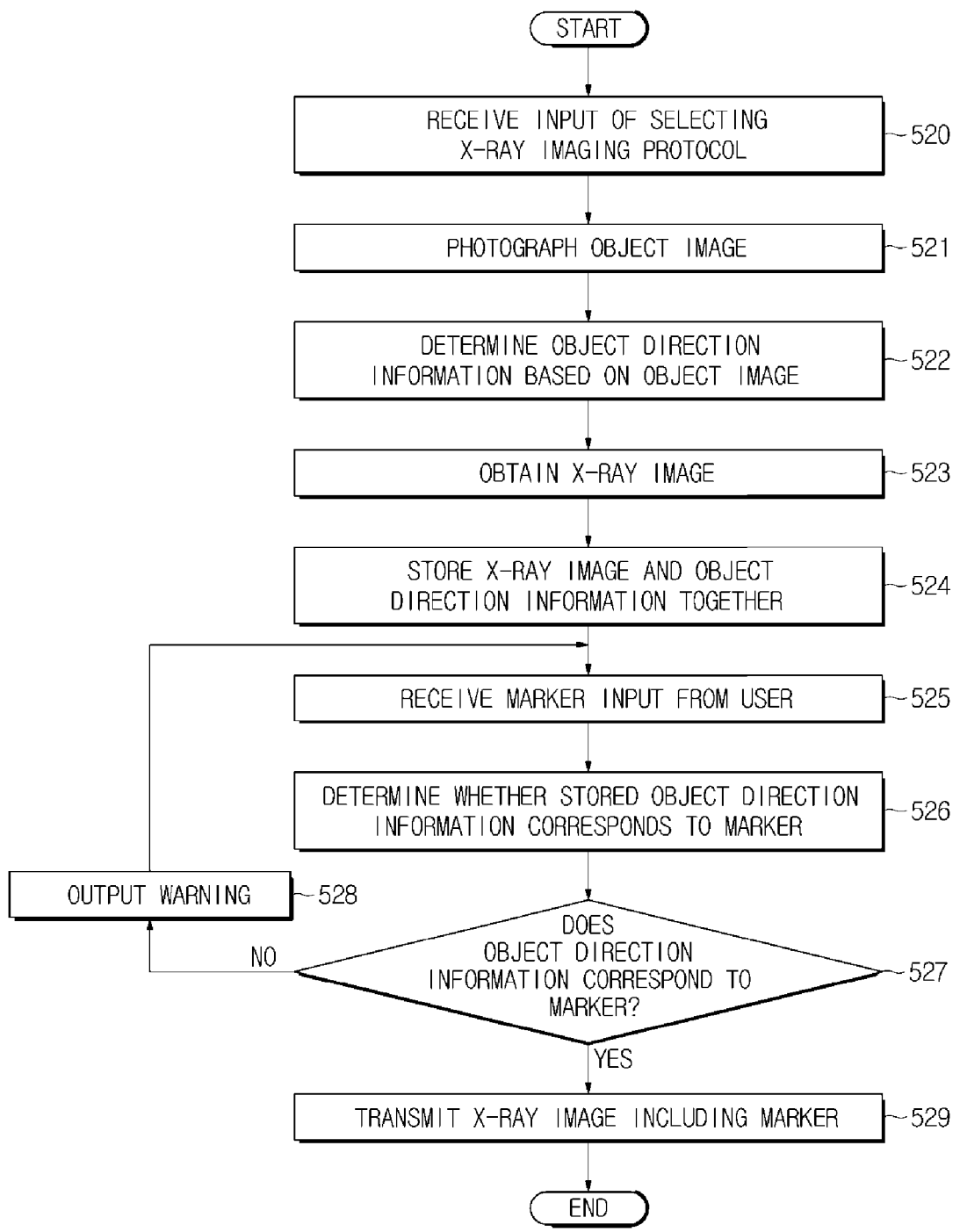
FIGS. 14 and 15 are flowcharts illustrating methods of displaying a marker in an X-ray image, in a method of controlling an X-ray imaging apparatus, according to an embodiment of the present disclosure.
Figure 15:
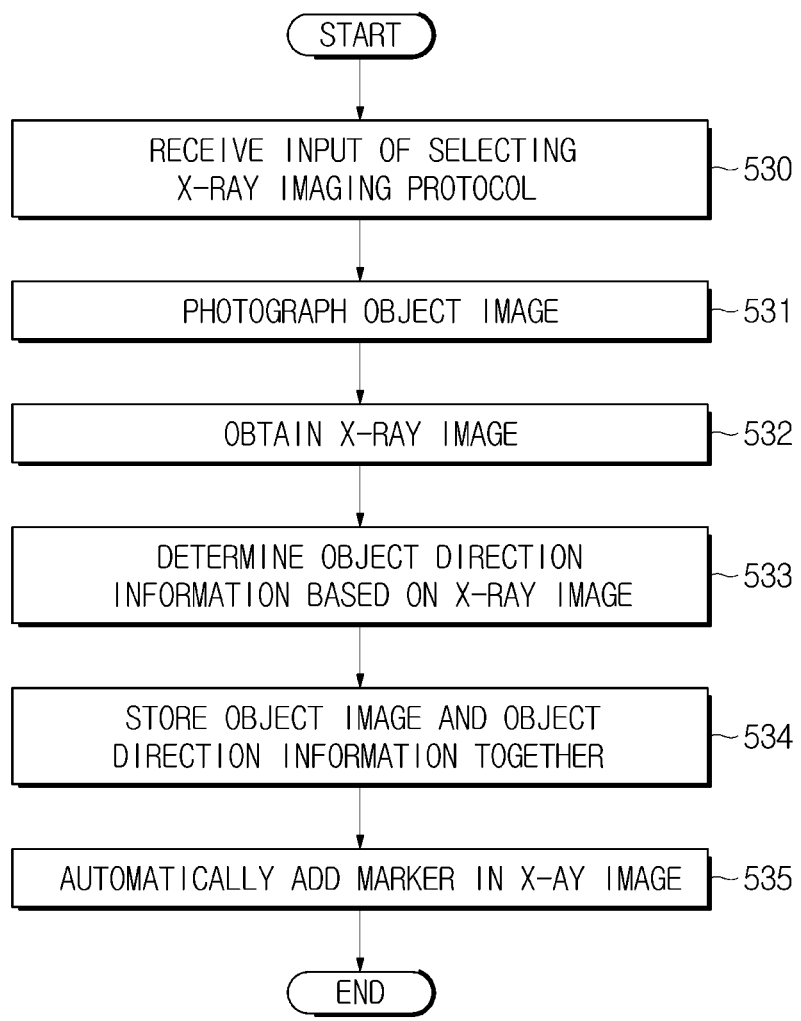

FIGS. 14 and 15 are flowcharts illustrating methods of displaying a marker in an X-ray image, in a method of controlling an X-ray imaging apparatus, according to an embodiment of the present disclosure.

Referring to FIG. 14, an input of selecting an X-ray imaging protocol may be received from a user, in operation 520, and an object image may be photographed, in operation 521. Then, object direction information may be acquired from the object image, in operation 522.

After the object direction information is acquired, it may be determined whether the object direction information corresponds to the X-ray imaging protocol, and a warning may be output according to the result of the determination, as described above with reference to FIG. 13. However, neither operation of determining whether the object direction information corresponds to the X-ray imaging protocol nor operation of outputting the warning may be performed.

Then, an X-ray image may be obtained, in operation 523. If the X-ray irradiator 110 irradiates X-rays onto the object, the X-ray detector 200 may detect X-rays transmitted through the object, and convert the X-rays into an electrical signal to acquire an X-ray image.

The X-ray image and the object direction information may be stored together, in operation 524. More specifically, information indicating an up, down, left, or right direction with respect to the object in the X-ray image, and information (that is, information indicating an AP image, a PA image, or a LAT image) indicating the front part, rear part, or lateral part of the object may be stored together.

Then, a marker input may be received from a user, in operation 525. A guide screen for allowing a user to input a marker may be displayed together with the X-ray image on the display unit 151. The user may select the kind or location of a marker through the input unit 152.

Then, it may be determined whether the stored object direction information corresponds to the marker, in operation 526. That is, it may be determined whether the kind and location of the marker input by the user correspond to the object direction information acquired from the X-ray image.

If the object direction information does not correspond to the marker ("No" in operation 527), a warning may be output for the user, in operation 528, and a marker input may be again received from the user.

If the object direction information corresponds to the marker ("Yes" in operation 527), an X-ray image including the marker may be transmitted, in operation 529. The X-ray image may be transmitted to PACS or to another external device (for example, a PC, a mobile device, etc.) registered in advance.

In the above-described example, a case in which a user himself/herself adds a marker in an X-ray image has been described, however, it is also possible to automatically display a marker in an X-ray image, as shown in FIG. 15, in operation 535. Since the controller 140 already knows the direction information of the object in the X-ray image, the controller 140 can automatically display a marker indicating the direction of the object in the X-ray image. Since operations from operation 530 of receiving an input of selecting an X-ray imaging protocol to operation 534 of storing an X-ray image and object direction information are the same as those from operation 520 to operation 524 of FIG. 14, detailed descriptions thereof will be omitted.

Figure 16:
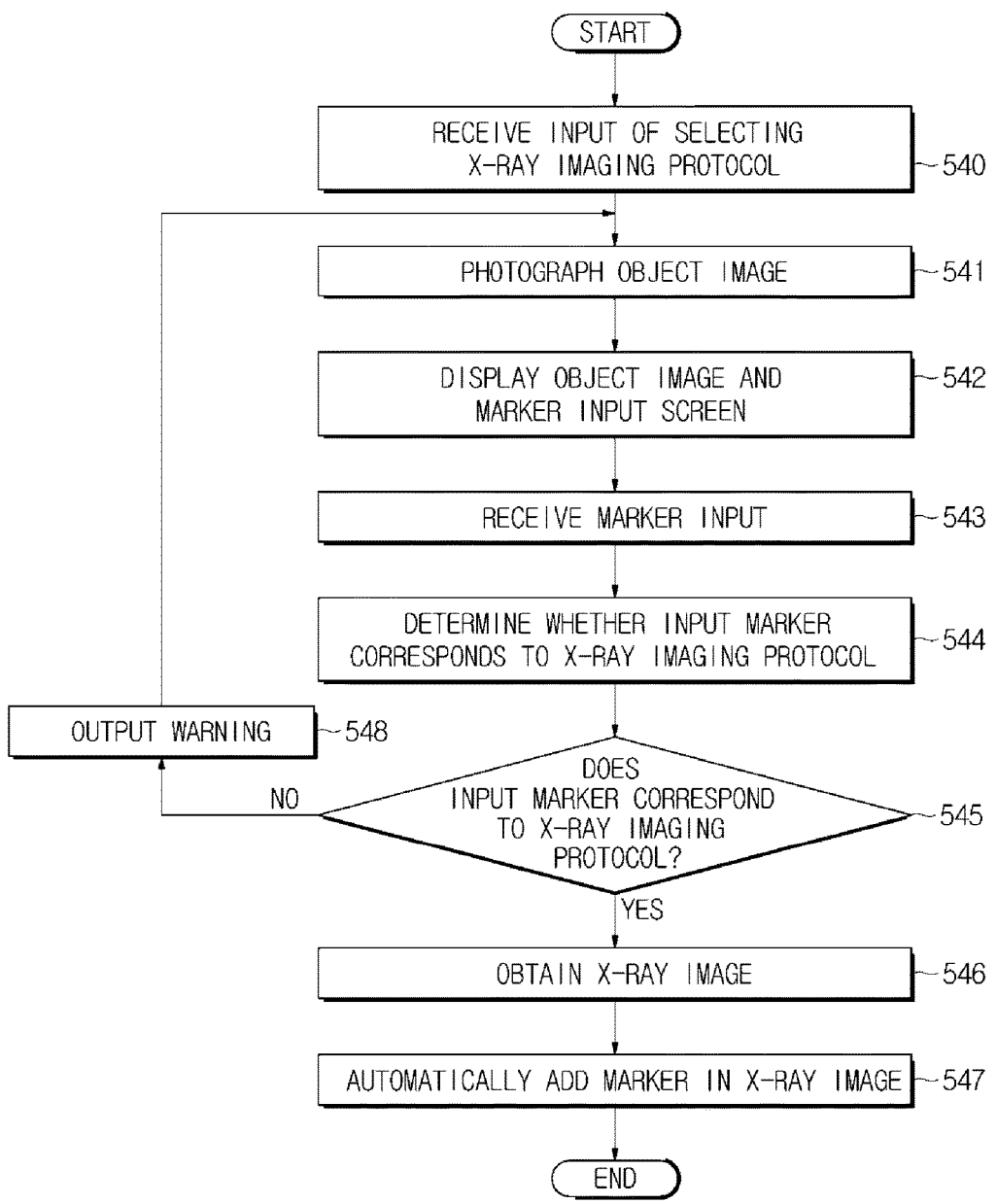
FIG. 16 is a flowchart illustrating a method of inputting a marker before radiography, in a method of controlling an X-ray imaging apparatus, according to an embodiment of the present disclosure.

FIG. 16 is a flowchart illustrating a method of inputting a marker before radiography, in a method of controlling an X-ray imaging apparatus, according to an embodiment of the present disclosure.

Referring to FIG. 16, an input of selecting an X-ray imaging protocol may be received from a user, in operation 540, and an object image may be photographed, in operation 541.

Then, the object image and a marker input screen may be displayed on the display unit 151, in operation 542. The configuration of the marker input screen is not limited as long as it can guide a user to select the kind or location of a marker. For example, as shown in FIG. 8, a marker display tool 151c for allowing a user to select the kind, location, and size of a marker may be displayed together with the object image.

Then, a marker input may be received from the user, in operation 543. The user may manipulate the input unit 152 to input information about the kind, location, or size of the marker. If the marker information is input, the marker may be displayed in the object image according to the input marker information.

Then, it may be determined whether the input marker corresponds to the X-ray imaging protocol, in operation 544. More specifically, the controller 140 may compare the input marker information to information about an irradiation direction of X-rays included in the selected X-ray imaging protocol.

If the input marker corresponds to the X-ray imaging protocol ("Yes" in operation), an X-ray image may be photographed, in operation 546.

Then, the marker may be automatically displayed in the X-ray image, in operation 547. More specifically, the controller 140 may display the marker in the X-ray image, based on the marker information input by the user before radiography and the selected X-ray imaging protocol. Accordingly, a process in which a user adds a marker after radiography can be omitted, and an error which may be generated when a user adds a marker while seeing an X-ray image from which he/she cannot easily determine the direction of an object can be prevented.

If the input marker does not correspond to the X-ray imaging protocol ("No" in operation 545), a warning may be output for the user, in operation 548. If the user realigns the location or position of the object, an object image may be again photographed, in operation 541.

Figure 17:
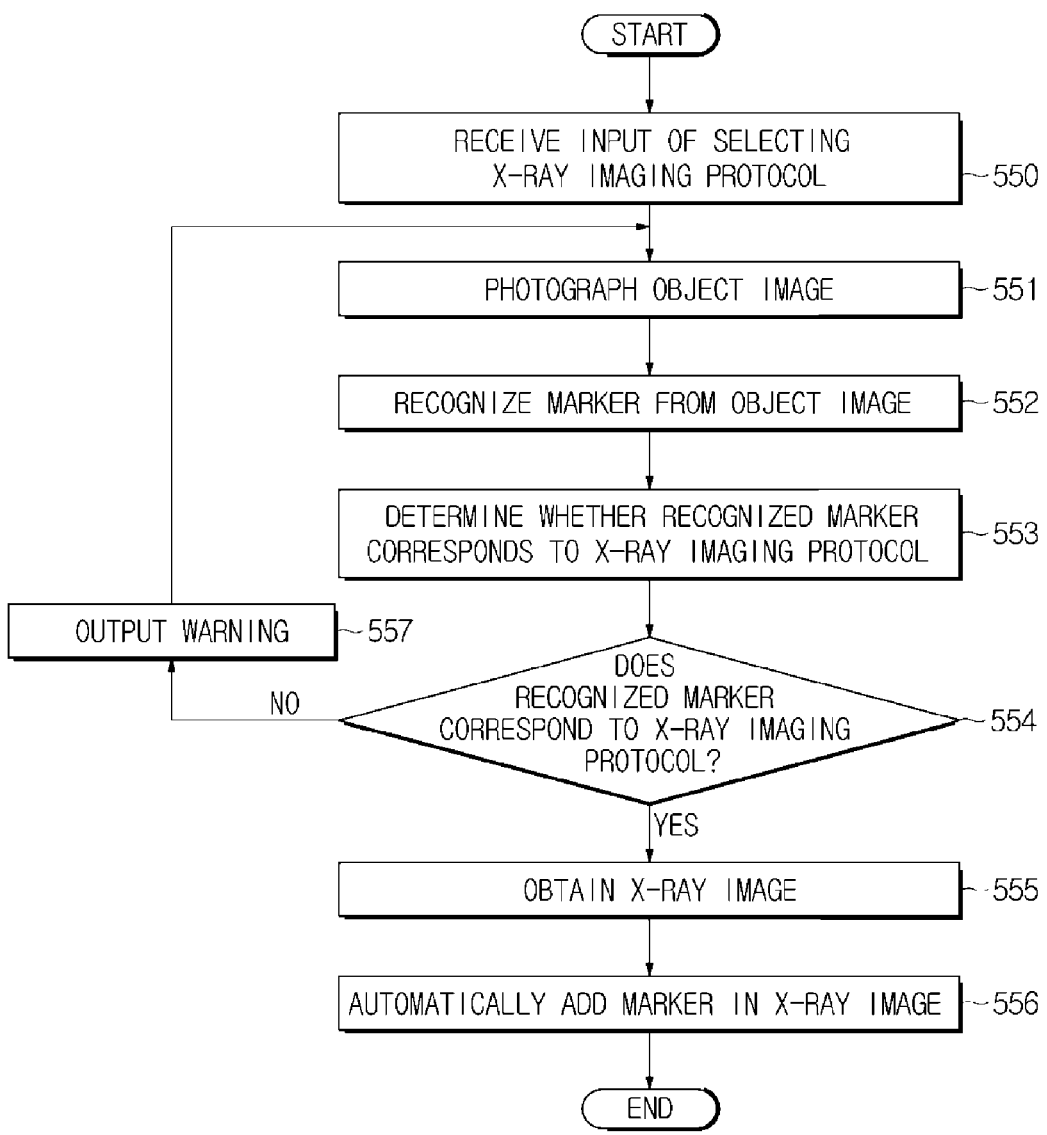
FIG. 17 is a flowchart illustrating a method of recognizing a hardware marker, in a method of controlling an X-ray imaging apparatus, according to an embodiment of the present disclosure.

FIG. 17 is a flowchart illustrating a method of recognizing a hardware marker, in a method of controlling an X-ray imaging apparatus, according to an embodiment of the present disclosure.

Referring to FIG. 17, an input of selecting an X-ray imaging protocol may be received from a user, in operation 550. Then, an object image may be photographed, in operation 551. Before the object image is photographed, the user may locate a hardware marker at a location adjacent to a photographing part of the object.

Then, the marker may be recognized from the object image, in operation 552. For this, features of the hardware marker, for example, the shape, color, pattern, etc. of the hardware marker may be stored in advance in the storage unit 170, and the controller 140 may apply one of various recognition algorithms to recognize the hardware marker appearing on the object image.

Then, it may be determined whether the recognized marker corresponds to the X-ray imaging protocol, in operation 553. The recognized marker information may include direction information of the object. The kind and location of the hardware marker may represent the direction information of the object. The controller 140 may compare the recognized marker information to information about an irradiation direction of X-rays included in the selected X-ray imaging protocol. If the controller 140 determines that the recognized marker information does not correspond to the information about the irradiation direction of X-rays ("No" in operation 554), the controller 140 may output a warning for the user, in operation 557. If the user realigns the location or position of the object and then locates the marker, an object image may be again photographed, in operation 551.

If the controller 140 determines that the recognized marker corresponds to the X-ray imaging protocol ("Yes" in operation 554), an X-ray image may be photographed, in operation 555, and a marker may be automatically displayed in the photographed X-ray image, in operation 556. The marker displayed in the X-ray image may be a software marker.

Then, the X-ray image including the software marker may be stored in the storage unit 170 or transferred to another external device such as PACS through the communication unit 170.

In the X-ray imaging apparatus and the control method thereof according to an aspect, by photographing a patient's image through a camera, determining information about the patient's direction based on the patient's image, or receiving information about the patient's direction from a user, and outputting a warning for the user if the information about the patient's direction does not correspond to an X-ray imaging protocol, it is possible to provide information about the patient's direction corresponding to an X-ray image.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. An X-ray imaging apparatus comprising:
an X-ray source configured to generate and radiate X-rays;
an imaging device configured to photograph an image of an object;
a controller configured to acquire object direction information from the photographed image of the object, and determine whether the object direction information corresponds to an imaging information included in an imaging protocol, the imaging information including at least one of a position of the object and a posture of the object; and
a user interface configured to output a warning in response to a determination by the controller that the object direction information does not correspond to the at least one of the position of the object and the posture of the object from the imaging protocol.

2. The X-ray imaging apparatus according to claim 1, wherein the controller is further configured to acquire the object direction information by determining at least one among an up direction, a down direction, a left direction, a right direction, a front direction, a rear direction, and a lateral direction, of the object, based on a feature of the object that is identified in the photographed image of the object.

3. The X-ray imaging apparatus according to claim 1, wherein the user interface comprises at least one among a display unit configured to visually output the warning, and a speaker configured to output the warning via a sound.

4. The X-ray imaging apparatus according to claim 1, wherein the imaging information included in the imaging protocol further includes an information about a radiation direction of the X-rays, the radiation direction being at least one among anteroposterior, posteroanterior, and lateral.

5. The X-ray imaging apparatus according to claim 1, wherein the controller is further configured to control the X-ray source to perform an X-ray imaging of the object in response to the determination by the controller that the object direction information corresponds to the imaging information included in the imaging protocol.

6. The X-ray imaging apparatus according to claim 5, wherein the controller is further configured to control the user interface to display a marker, which indicates a direction of the object, in an X-ray image, based on the object direction information.

7. The X-ray imaging apparatus according to claim 5, wherein the user interface comprises:
a display configured to display an X-ray image of the object; and
an input unit configured to receive an input for displaying a marker which indicates a direction of the object in the X-ray image.

8. The X-ray imaging apparatus according to claim 7, wherein the controller is further configured to output the warning on the display in response to a determination by the controller that the direction of the object indicated by the marker does not correspond to the object direction information.

9. An X-ray imaging apparatus comprising:
an X-ray source configured to generate and radiate X-rays;
an imaging device configured to photograph an image of an object;
a display configured to display the photographed image of the object; and
an input unit configured to receive an input for displaying a first marker, which indicates a direction of the object, in the photographed image of the object, before the X-ray source radiates the X-rays to capture an X-ray image of the object.

10. The X-ray imaging apparatus according to claim 9, further comprising a controller configured to determine whether the direction of the object indicated by the first marker corresponds to information about a radiation direction of the X-rays,
wherein the display is further configured to output a warning in response to a determination by the controller that the direction of the object indicated by the first marker does not correspond to the information about the radiation direction of the X-rays.

11. The X-ray imaging apparatus according to claim 9, further comprising a controller configured to display a second marker, which indicates the direction of the object, in the X-ray image, based on the direction of the object indicated by the first marker displayed in the photographed image of the object.

12. The X-ray imaging apparatus according to claim 9, further comprising a controller configured to acquire object direction information from the photographed image of the object, and output a warning via the display in response to a determination that the direction of the object indicated by the first marker does not correspond to the object direction information.

13. A method of controlling an X-ray imaging apparatus, the method comprising:
photographing an image of an object;
acquiring object direction information from the photographed image of the object;
determining whether the object direction information corresponds to imaging information included in an imaging protocol, the imaging information including at least one of a position of the object and a posture of the object; and
outputting a warning in response to the determining that the object direction information does not correspond to the at least one of the position of the object and the posture of the object from the imaging protocol.

14. The method according to claim 13, wherein the acquiring the object direction information from the photographed image of the object comprises:
determining at least one among an up direction, a down direction, a left direction, a right direction, a front direction, a rear direction, and a lateral direction of the object, based on a feature of the object that is identified in the photographed image of the object.

15. The method according to claim 13, further comprising:
capturing an X-ray image of the object by radiating X-rays with an X-ray source and detecting the X-rays with a detector; and
displaying a marker, which indicates a direction of the object, in the X-ray image, based on the object direction information.

16. The method according to claim 13, further comprising:
capturing an X-ray image of the object by radiating X-rays with an X-ray source and detecting the X-rays with a detector;
displaying the X-ray image; and
receiving an input for displaying a marker, which indicates a direction of the object, in the X-ray image.

17. The method according to claim 16, further comprising:
outputting a warning via a user interface in response to the determining that the direction of the object indicated by the marker does not correspond to the object direction information.

18. The X-ray imaging apparatus according to claim 1, wherein the controller is further configured to control the X-ray source to perform an X-ray imaging of the object after the controller determines that the object direction information corresponds to the at least one of the position of the object and the posture of the object from the imaging protocol.

19. The X-ray imaging apparatus according to claim 1, wherein the imaging information included in the imaging protocol further includes information about an area of the object where the X-rays are to be irradiated by the X-ray source, and
the controller is further configured to determine whether the object direction information corresponds to the area of the object from the imaging protocol.

20. The X-ray imaging apparatus according to claim 19, wherein the controller is further configured to acquire the object direction information by determining at least one among an up direction, a down direction, a left direction, and a right direction, of the object, based on a feature of the object that is identified in the photographed image of the object, and compare the at least one among the up direction, the down direction, the left direction, and the right direction with the information about the area of the object from the imaging protocol.

21. An X-ray imaging apparatus comprising:
an X-ray source configured to generate and radiate X-rays;
an imaging device configured to photograph an image of an object;
a controller configured to acquire object orientation information from the photographed image of the object, and determine whether the object orientation information corresponds to imaging information included in an imaging protocol, the imaging information including at least one of a position of the object and a posture of the object; and a user interface configured to output a warning in response to a determination by the controller that the object orientation information does not correspond to the at least one of the position of the object and the posture of the object from the imaging protocol.

22. An X-ray imaging apparatus comprising:
an X-ray source configured to generate and radiate X-rays;
an imaging device configured to photograph an image of an object;
an input unit configured to receive an input of an imaging protocol selected by a user;
a controller configured to acquire object direction information from the photographed image of the object, and determine whether the imaging protocol corresponds to the object direction information; and
a user interface configured to output a warning based on a determination by the controller that the object direction information does not correspond to the imaging protocol.

* * * * *